United States Patent [19]

Deshmukh

[11] 4,042,330

[45] Aug. 16, 1977

[54] IN A METHOD FOR CHECKING THE ACCURACY OF A TEST USING AN ENZYMATICALLY HYDROLYZABLE, SERUM-SOLUBLE CHOLESTEROL COMPOUND

[76] Inventor: Arvind D. Deshmukh, 1011 Pearl St., Santa Monica, Calif. 90405

[21] Appl. No.: 716,616

[22] Filed: Aug. 23, 1976

[51] Int. Cl.² ........................................... G01N 33/16
[52] U.S. Cl. ................................................ 23/230 B
[58] Field of Search ...................................... 23/230 B

[56] References Cited

U.S. PATENT DOCUMENTS 3,859,047  1/1975  Klein .................................. 23/230 B Primary Examiner—Robert M. Reese
Attorney, Agent, or Firm—Nilsson, Robbins, Dalgarn & Berliner

[57] ABSTRACT

Water and serum soluble cholesterol compounds are prepared by reactively combining certain esters of cholesterol with a solubilizing agent selected from the group consisting of peptides, proteins, water soluble polycarboxylic acids, organic and inorganic water soluble salts of said polycarboxylic acids, and cis-vicinal water-soluble polysaccharides. The water-soluble cholesterol compounds can be lyophilized and added to serum as a standard for the determination of cholesterol in biological fluids either by traditional saponofication methods or by enzymatic methods.

9 Claims, No Drawings

IN A METHOD FOR CHECKING THE ACCURACY OF A TEST USING AN ENZYMATICALLY HYDROLYZABLE, SERUM-SOLUBLE CHOLESTEROL COMPOUND

FIELDS OF THE INVENTION

The fields of art to which the invention pertains include the field of steroid chemistry and the field of biological testing.

BACKGROUND AND SUMMARY OF THE INVENTION

In recent years, it has become common in clinical laboratories to test for the level of cholesterol in blood serum samples. The measured levels of cholesterol in the blood are referred to as total serum cholesterol, and include all those cholesterol compounds which are present in the blood such as cholesterol and its derivatives dihydrocholesterol and 7-dihydrocholesterol, whether present in their free form or in the form or esters with the fatty acids normally present in the blood. There are a number of methods which can be utilized for the determination of total cholesterol in biological fluids. In accordance with the method of Abell et al, the serum is treated with alcoholic potassium hydroxide to liberate the cholesterol from its lipoprotein complexes and to saponify the natural cholesterol esters. The saponified cholesterol is extracted into a measured volume of petroleum ether and then an aliquot is subjected to color reaction utilizing a modified Libermann-Burchard reagent. Reference can be made to the journal "STANDARDIZED METHODS OF CLINICAL CHEMISTRY", vol. 2, pages 26 etc. (1958) by L. L. Abell et al. The optical density of each sample is read against a blank in a photoelectric colorimeter. The level of cholesterol equivalent to the optical density is calculated by comparing the optical density to that of a standard containing a known amount of cholesterol.

For most serum clinical chemistry procedures, it is desirable to use one serum based reference control for a variety of tests. However, cholesterol, per se, is not soluble in biological fluids such as serum. To overcome such deficiency, the prior art has attempted to solubilize the cholesterol by forming organic salts thereof. See, for example, U.S. Pat. No. 3,859,047 to Klein. However, the level of solubility achieved is insufficient to provide sufficiently high concentrations for all desired uses. For example, even with the use of a surfactant such as Triton X-100 (polyethyleneglycol ether of monoisoocytyl phenol, by Rohm & Haas, Inc., Philadelphia, Pa.) a useful concentration of less than 0.1 gram per deciliter is provided. The sample becomes turbid at significantly higher concentrations, and since a colorimetric procedure is utilized, gross errors can be introduced.

More recently, a method for cholesterol analysis employing the enzyme cholesterase has been developed and has been increasingly used in analytical laboratories. Accordingly, it will be desirable for a cholesterol standard to be useful not only in the saponification chemistry of the Abell et al method but also in the enzymatic procedures.

The present invention provides serum-soluble cholesterol compounds and methods for their preparation, which can be lyophilized and added in high concentration to blood serum. A turbid-free clinical chemistry control is thus provided having a high cholesterol value and which can be assayed by the standard or enzymatic procedures. Concentration levels of up to 1 gram of cholesterol equivalent per deciliter are easily prepared. Furthermore, the cholesterol compounds of this invention do not interfere with other analytical tests making them highly useful in a multiple serum control.

More specifically, the present cholesterol compounds are defined by certain esters of cholesterol reactively combined with a solubilizing agent selected from the group consisting of peptides, proteins, water-soluble polycarboxylic acids, organic and inorganic water-soluble salts of said acids, and cis-vicinal water-soluble polysaccharides. With regard to the peptides and proteins, reaction is with the amino groups derived therefrom (i.e., as a part thereof). The ester can be: (A) an acid ester of cholesterol, in which the acid group has at least six carbon atoms in its longest chain (including the acid carbon atoms), reactable with the amine component of the peptide or protein amino residue; or (B) an amino ester of cholesterol reactable (1) directly with the acid portion of the peptide or protein amino residue or with the polycarboxylic acid, (2) indirectly through a phosgene or thiophosgene coupling agent with the amine component of the peptide or protein amino residue, or (3) indirectly through a cyanogen halide with a polysaccharide.

DETAILED DESCRIPTION

As an initial step in the preparation of a water soluble, serum-soluble cholesterol compound useful herein, there is first formed an ester of cholesterol which can be an acid ester or an amino ester, having, respectively, the following formulas:

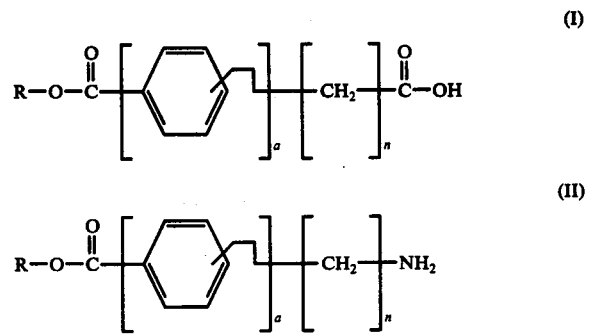

in which R is a cholesteryl radical, $a$ is 0 or 1, $n$ is 4–30 in formula I and is 1–30 in formula II. The above esters can be prepared by reacting cholesterol with the corresponding dibasic acid or amino acid. Examples of alkyl or aryl monoacid esters of formula (I) include cholesteryl hydrogen phthalate, cholesteryl hydrogen suberate, cholesteryl hydrogen dodecanediate, and the like. Compounds such as those provided herein which are formed from acid esters of cholesterol in which the acid portion contains five or less carbon atoms in its longest chain (including the acid carbon atoms) are generally not enzymatically hydrolyzable. The first example can be purchased from Aldrich Chemical Co. Examples of alkyl or aryl monoamino esters of Formula (II) include cholesteryl-6'-aminohexanoate, cholesteryl-12'-aminododecanate, cholesteryl-4'-aminobenzoate, and the like.

The acid ester of cholesterol of formula (I) can be reacted directly with the amine component of the amino residue of a protein or peptide in accordance with the following equation.

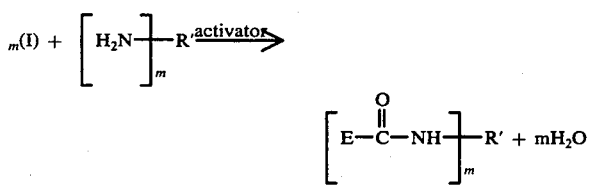

in which $m$ is 1 to 100, $R'$ is from a peptide or protein having the amino residue $R'—NH_{2m}$, and E is the cholesteryl ester function:

The amino group is from a peptide, preferably a high molecular weight peptide, or from a protein, and in this regard it is particularly preferred to use albumin, such as human, rabbit or bovine albumin, but preferably the latter. Bovine albumin has 59 lysine residues, permitting a large number of cholesterol radicals to be conjugated therewith. Broadly, materials such as polylysine, polyarginine, small peptides having 6 or more amino acids and which contains basic groups (e.g. lysine) as a constituent, can all be used. Reference can be made to "Biological Chemistry", by H. R. Mahler and E. H. Cordes, Harper Row Pub., N.Y., pages 9–120, for a description of suitable peptides, which description is incorporated herein by reference.

In conducting the foregoing reaction, an activating agent should be used and such be defined as a material which facilitates reaction between an acid and an amine and which has minimum reaction with cholesterol. Such materials are well known in the field of protein and peptide synthesis and one can refer to "BASIC PRINCIPLES OF ORGANIC CHEMISTRY" by Roberts and Cassiero, (1964), pages 702–723, published by W. A. Benjamin, Inc., incorporated herein by reference. Specific examples include carbodiimides such as dicyclohexyl carbodiimide, 1-ethyl-3-(3'-dimethylaminopropyl) carbodiimide, Woodward Reagent K-(N-ethyl-5-phenylisoxazolium-3'-sulfate), alkylchloroformate such as ethylchloroformate, n-butylchloroformate, isobutylchloroformate, and the like.

The amino ester of cholesterol of Formula (II) can be reacted directly with the acid portion of the amino residue of a protein or peptide in accordance with the following equation:

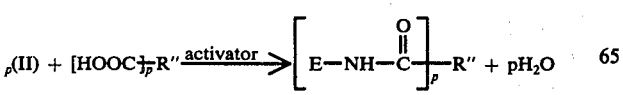

in which $p$ is 1 to 100, and $R''$ is derived from the high molecular weight amino acid

as indicated, an activator is used and the reaction is conducted in a water miscible organic solvent. The amino residue and the activator can each be identical to that described move with respect to the acid ester of cholesterol of Formula (I).

The amino ester of cholesterol of Formula (II) can be reacted directly with a water-soluble polycarboxylic acid polymer, in accordance with the following exemplary equation:

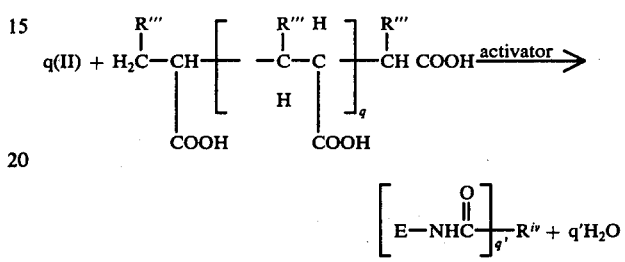

in which $q$ is 2–500,000 or higher, $q'$ is 2% –50% of $q$, $R'''$ is hydrogen, methyl or ethyl and $R^{iv}$ is the remaining portion of said polycarboxylic acid.

The polycarboxylic acids are preferably those which have at least one -COOH group per 20 carbon atoms of skeletal structure, and particularly useful materials are the polyacrylic and polymethacrylic acids. Water soluble, inorganic salts such as those of potassium, sodium, calcium and the like are also useful as are the water-soluble organic salts. The latter salts can be obtained by reaction with an organic base such as morpholine, cyclohexylamine and tris (hydroxymethyl) aminomethane. See, in this regard, the organic bases referred to by Klein U.S. Pat. No. 3,859,047, incorporated herein by reference.

The amino ester of cholesterol of Formula (II) can be reacted by means of a cyanogen halide coupling reagent with a cis-vicinal, water-soluble polysaccharide in accordance with the following equation:

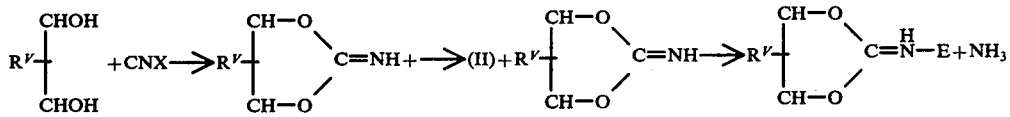

in which X is halogen such as chlorine or bromine and

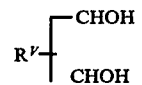

is a cis-vicinal, water-soluble polysaccharide.

The amino ester of cholesterol of Formula (II) can be reacted by means of a phosgene coupling reagent with the amine component of the amino residue of a protein or peptide in accordance with the following equations:

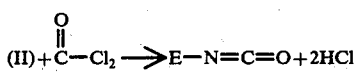

-continued

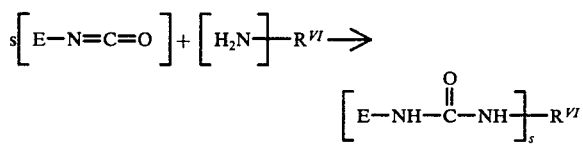

in which s is 1 to 100 and $R^{VI}$ is derived from the high molecular weight amino acid

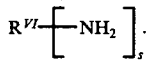

In like manner, the amino ester of cholesterol of Formula (II) can be reacted by means of a thiophosgene coupling reagent with the amine component of the amino residue of a protein or peptide in accordance with the following equation:

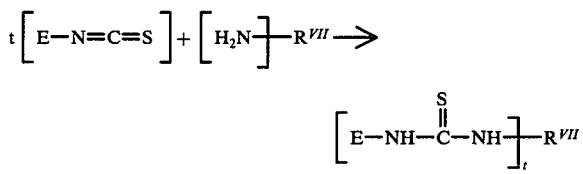

in which t is 1 to 100 and $R^{VII}$ is derived from the high molecular weight amino acid

In the above reactions involving phosgene or thiosphosgene, the high molecular weight amino acid can be the same as described above with respect to reaction of the acid ester of cholesterol of Formula (I).

In each of the foregoing preparations, the peptide, protein or polysaccharide can be dissolved in distilled water and a water-miscible organic solvent added thereto, such as dimethylsulfoxide, dimethyl formamide, tetrahydrofuran, acetone, dioxane, acetonitrile, or the like. The cholesterol ester component and activating agent or coupling reagent can then be added to the well mixed solution. The resultant solution can be dialyzed against running water for several days followed by lyophilization to produce a powdery material. In general, it is desirable to conduct the reaction between the peptide, protein or polysaccharide and cholesterol ester component under alkaline conditions. Accordingly, a small amount of sodium hydroxide or the like can be added to the reaction solution.

The resultant lyophilized substances can form stable aqueous solutions which dissolve in biological fluids such as whole serum to form clear, stable solutions yielding accurate, positive results with both saponification and enzymatic test procedures. The consistency of results is unaffected by other substances normally present in biological fluids and the cholesterol compounds of the invention when added to biological fluids such as serum, do not interfere with other analytical tests usually carried out thereon thus making them highly useful as a cholesterol member of multiple component analytical standards and control materials. Advantageously, the cholesterol compounds of the invention are readily soluble in water in an amount equivalent to about 10 grams of cholesterol equivalent per 100 milliliter, and in biological fluids such as cholesterolfree serum in an amount equivalent to about 7 grams of free cholesterol per 100 milliliters. For common analytical procedures, an amount of cholesterol compound equivalent to form about 50 milligram to about 400 milligram of cholesterol per 100 milliliter, dissolved in 5 ml. water is used to reconstitute a lyophilized 5 sample of the biological fluid to be tested. These amounts are chosen as they represent the practical levels of cholesterol in the blood. Aliquots are from 0.10 to 0.50 ml. of the reconstituted serum are utilized as standards for most analytical procedures. The cholesterol compounds of the present invention may be supplied per se in dry form or as standard stock solutions.

In the foregoing formulations, conjugated cholesterol compounds and cholesterol esters have been described wherein a is 0 or 1 and n is 4–30 for acid esters and is 1–30 for amino esters. It is preferred to use such compounds and esters in which a is 1, n is derived from a lower alkyl group, i.e., n is 1–5 and, when a is 0, n is derived from a higher alkyl group, i.e., n is 4–30. Most preferably, a is 0 and n is derived from a fatty acid group of 12–20 carbon atoms. Esters wherein a is 1 or wherein a is 0 and n is 4–30 are believed to be new compositions of matter.

The following examples further illustrate the invention.

EXAMPLE 1

25.8 Grams of dodecandeicarboxylic acid was dissolved in 350 ml. toluene and placed in a three-necked flask equipped with an addition funnel, mechanical stirrer and a Dean Stark water separator. 0.1 Grams of toluene sulfonic acid (catalytic amount) was added to the well-stirred solution. 38.7 Grams of cholesterol, dissolved in 150 ml. toluene, was introduced dropwise to the refluxing solution. After the addition was complete, the mixture was continually heated for an additional twenty-four hours. Solvent was removed under vacuum. The dried material was dissolved in a minimum amount of tetrahydrofuran and separated as the major component on a silica gel chromatography column to yield the desired product.

EXAMPLE 2

20.1 Grams of 12-aminododecanoic acid can be reacted with 20.4 grams of carbobenzyl chloride to yield the N-protected amino acid. 15 Grams of the protected compound can then be dissolved in 250 ml. tetrahydrofuran and reacted with dicyclohexylcarbodiimide. The activated acid can then be reacted with cholesterol in equal molar concentrations to form the desired ester. The protection group can then be removed by hydrogenolysis.

EXAMPLES 3–5

The procedure of Example 2 can be followed but substituting respectively molar equivalent amounts of 6-aminocaproic acid for the 12-aminododecanoic acid, p-(B-aminoethyl)benzoic acid or p-(70 aminoheptanyl)-benzoic acid for the 12-aminododecanoic acid.

EXAMPLE 6

3.6 grams of bovine serum albumin was dissolved in 94 ml. deionized water. 90 parts of dimethylformamide (DMF) was then introduced along with 4 ml. of 6 N sodium hydroxide.

1.6 grams of cholesteryl hydrogen dodecanedicarboxylate were dissolved in DMF. The resulting solution was cooled by insertion into an ice bath. Then 0.556 ml. tributylamine was added, followed by 0.4 ml. of isobutylchloroformate. This solution was stirred for 20 minutes at 4° C. The activated material was then added to the albumin solution. The resulting solution was continously mixed for 6 hours at ambient temperature. A product was obtained by dialyzing for 48 hours against distilled water followed by lyophilization.

EXAMPLE 7

The procedure of Example 6 can be followed but substituting a molar equivalent amount of cholesteryl hydrogen phthalate for the cholesteryl hydrogen dodecanedicarboxylate.

EXAMPLE 8

20 grams of polyacrylic acid, in the form of a 25 weight percent aqueous solution, can be mixed with a water soluble carbodiimide, in a ¼ molar ratio. After 30 minutes cholesteryl-12 -aminododecanoate, in molar ratio to the carbodiimide, dissolved in dimethylformamide can be introduced. This material can then be stirred for 6 hours, dialyzed against running distilled water for 48 hours and lyophilized to yield the desired product.

EXAMPLES 9 and 10

The procedure of Example 8 can be followed but substituting respectively molar equivalent amounts of cholesteryl p-(B-aminoethyl)benzoate or p-7 -aminoheptanyl benzoate.

EXAMPLE 11

3.6 grams of bovine serum albumine (BSA) can be dissolved in 94 mls. deionized water to which solution is added 90 mls. DMF followed immediately by 4 mls. 6 N NaOH. In another vessel with 10 ml. DMF, 3.0 millimolar thiophosgene can be reacted with 1.6 grams aminocholesterol by stirring for 30-60 minutes. This solution can then be added to the BSA solution and allowed to react for four hours while maintaining an alkaline pH. of 9.0 to 11.0 by appropriate addition of 6 N NaOH. The mixed solution can then be dialyzed for 48-72 hours against running water, and the resulting dialyzate frozen and lyophilized, to yield the desired product.

EXAMPLE 12

1.9 grams of aminocholesterol derivative can be solubilized in 20 mls. of 75% DMF and adjusted to a pH 11.0 by addition of 6 N NaOH.

3.0 millimolar amylodextrin can be dissolved in another reagent vessel. The pH can then be rapidly adjusted to 11.0 with 6 N NaOH and the material allowed to sit 3 hours at ambient temperature. In an appropriate hood, 318 mg. of CNBr in 10 mls. 50% DMF can be added and allowed to react for 30 minutes while the pH is maintained at 11.0.

The cholesteryl solution can then be added to the resultant CNBr amylodextrin solution and allowed to react while maintaining the pH at 11.0 until the pH stabilizes. This solution can then be dialyzed against running water in a hood for 48-72 hours, then frozen and lyophilized to yield the desired product.

EXAMPLE 13

In a non-enzymatic method of test, 1.5 Grams of the cholesterol dodecanedicarboxalate were added to an assayed control serum with a cholesterol value of 110 msg%. Values before and after addition of the cholesterol reagent described in examples 108, 429 by the Kilaney Zak (Standard Methods in Clinical Chemistry, Ed. Meites, S. Academic Press N.Y. 1965, vol. 5, p. 79 ) procedure are as follows:

| Before Addition | After Addition | % Recovery |
| --- | --- | --- |
| 108 | 429 | 98 |

The cholesterol additive in the above cases gave a % C.V. of 2.8, as used in the method described.

EXAMPLE 14

The lyophilized cholesterol conjugate was assayed by the enzymatic procedure outlined in the Boehringer-Mannheim product (cholesterol test cat. no. 015732 ).

1.5 Grams of synthesized cholesterol conjugate were added to normal assayed human serum controls and magnetically stirred to dissolve the conjugate. In each case of addition of the cholesterol conjugate, the expected 330 mgs% increase in the cholesterol value was within + or − 8%. For example, in the case where the cholesterol conjugate is described in example no. 6, 0.375 Grams of cholesterol dodecandedicarboxylate were added to 25.0 ml. of 110 mg% assayed control serum. The calculated increase and the observed increase by the enzymatic method of B-M are described in the following table:

| Determination No. | Calculated Increase | Observed Increase | % Recovery |
| --- | --- | --- | --- |
| 1 | 330 | 328 | 99 |
| 2 | 330 | 335 | 102 |
| 3 | 330 | 340 | 103 |

I claim:

1. In a method for checking the accuracy of a test for the quantitative determination of the cholesterol content of a biological fluid wherein said test is conducted on a standard comprising a solution in said biological fluid of a known quantity of a serum-soluble cholesterol compound, the improvement in accordance with which said cholesterol compound is at least one ester of cholesterol reactively combined with a solubilizing agent selected from the group consisting of peptides, proteins, water-soluble polycarboxylic acids, organic and inorganic water-soluble salts of said polycarboxylic acids, and cis-vicinal water-soluble polysaccharides, said ester of cholesterol being selected from the (a) esters of an acid having at least six carbon atoms in its longest chain, and (b) amino esters.

2. The improvement of claim 1 in which said cholesterol compound has as a functional component of said ester

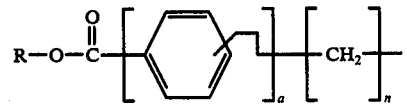

in which R is a cholesteryl radical, $a$ is 0 or 1, and $n$ is 1–30.

3. The improvement of claim 2 wherein said cholesterol compound has the formula

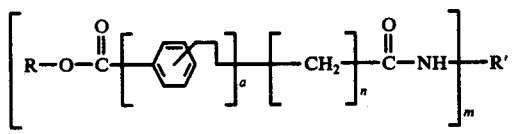

in which $n$ is at least 4, $m$ is 1 to 100 and

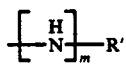

is derived from a peptide or protein having the amino residue

4. The improvement of claim 2 wherein said cholesterol compound has the formula

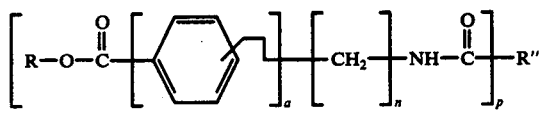

in which $p$ is 1 to 100 and

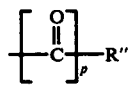

is a peptide or protein having the amino residue

5. The improvement of claim 2 wherein said cholesterol compound has the formula

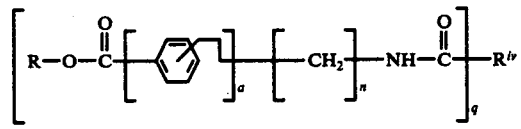

in which $q$ is at least 2 and $R^{iv}$ is the remaining portion of a water-soluble polycarboxylic acid molecule.

6. The improvement of claim 2 wherein said cholesterol compound has the formula

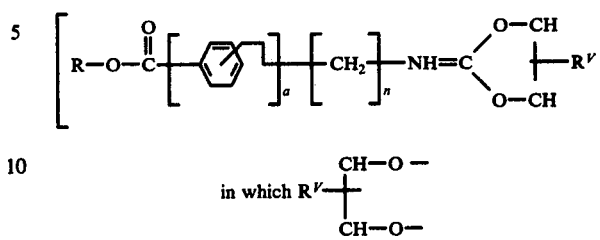

is a divalent radical of a cis-vicinal, water-soluble polysaccharide.

7. The improvement of claim 2 wherein said cholesterol compound has the formula

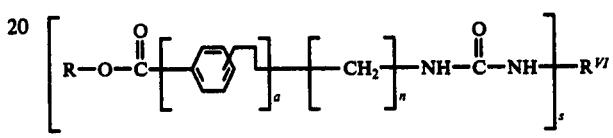

in which $s$ is 1 to 100 and

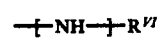

is a peptide or protein having the amino residue

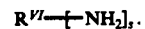

8. The improvement of claim 2 in which said cholesterol compound has the formula

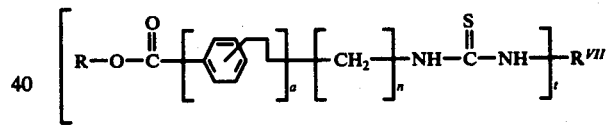

in which $t$ is 1 to 100 and

is a peptide or protein having the amino residue

9. The improvement of claim 2 wherein $n$ is 4–20.

* * * * *

UNITED STATES PATENT AND TRADEMARK OFFICE
CERTIFICATE OF CORRECTION

PATENT NO. : 4,042,330
DATED : August 16, 1977
INVENTOR(S) : Arvind D. Deshmukh

It is certified that error appears in the above-identified patent and that said Letters Patent are hereby corrected as shown below:

Col. 3, line 14, "$R'-NH_{2m}$" should be --$R'-NH_{2_m}$--.

Col. 3, line 37, "such be" should be --such can be--.

Col. 4, line 5, "as indicated" should be --As indicated--.

Col. 4, line 8, "move" should be --above--.

Signed and Sealed this

Sixth Day of December 1977

[SEAL]

Attest:

RUTH C. MASON
*Attesting Officer*

LUTRELLE F. PARKER
*Acting Commissioner of Patents and Trademarks*

Disclaimer 4,042,330.—*Arvind D. Deshmukh*, Santa Monica, Calif. IN A METHOD FOR CHECKING THE ACCURACY OF A TEST USING AN ENZYMATICALLY HYDROLYZABLE, SERUM-SOLUBLE CHOLESTEROL COMPOUND. Patent dated Aug. 16, 1977. Disclaimer filed May 12, 1978, by the inventor.

The term of this patent subsequent to Aug. 9, 1994, has been disclaimed.

[*Official Gazette July 4, 1978.*]